United States Patent
Thomson et al.

(10) Patent No.: US 10,429,275 B2
(45) Date of Patent: Oct. 1, 2019

(54) TRACE ANALYTE COLLECTION SWAB

(71) Applicant: Smiths Detection Montreal Inc., Mississauga (CA)

(72) Inventors: Paul Christopher Peter Thomson, Mississauga (CA); Atin J. Patel, Mississauga (CA)

(73) Assignee: Smiths Detection Montreal Inc., Mississauga, Ontario (CA)

( * ) Notice: Subject to any disclaimer, the term of this patent is extended or adjusted under 35 U.S.C. 154(b) by 68 days.

(21) Appl. No.: 14/778,293

(22) PCT Filed: Mar. 10, 2014

(86) PCT No.: PCT/CA2014/050200
§ 371 (c)(1),
(2) Date: Sep. 18, 2015

(87) PCT Pub. No.: WO2014/146197
PCT Pub. Date: Sep. 25, 2014

(65) Prior Publication Data
US 2016/0202149 A1 Jul. 14, 2016

Related U.S. Application Data

(60) Provisional application No. 61/802,890, filed on Mar. 18, 2013.

(51) Int. Cl.
*G01N 1/04* (2006.01)
*G01N 1/28* (2006.01)
(Continued)

(52) U.S. Cl.
CPC ............... *G01N 1/04* (2013.01); *B01L 3/505* (2013.01); *B42D 5/00* (2013.01); *G01N 1/02* (2013.01);
(Continued)

(58) Field of Classification Search
CPC ............... G01N 1/04; G01N 2001/024; G01N 2001/028; B01L 3/505; B01L 2200/148; B01L 2300/0825; B42D 5/00
(Continued)

(56) References Cited

U.S. PATENT DOCUMENTS 5,243,864 A * 9/1993 Dunmyre ............. G01N 1/2214
73/864.71
5,462,063 A 10/1995 Kist et al.
(Continued)

FOREIGN PATENT DOCUMENTS

AU 619413 B2 1/1992
CA 2218785 4/1998
(Continued)

OTHER PUBLICATIONS

Office Action dated Mar. 21, 2017 for Chinese Appln. No. 201480016770.3.
(Continued)

*Primary Examiner* — Nimeshkumar D Patel
*Assistant Examiner* — Marrit Eyassu
(74) *Attorney, Agent, or Firm* — Kevin E. West; Advent, LLP

(57) ABSTRACT

A trace analyte collection swab having a collection surface at least partially coated with a microscopically tacky substance to enhance pick-up efficiency is described. In embodiments, the trace analyte collection swab comprises a substrate including a surface having a trace analyte collection area and a coating disposed on the surface of the substrate in the trace analyte collection area. The coating is configured to be microscopically adhesive to collect particles of the trace analyte from a surface when the trace analyte collection area is placed against the surface. In one embodiment, the coating comprises Polyisobutylene.

18 Claims, 6 Drawing Sheets

(51) Int. Cl.
  *G01N 1/02* (2006.01)
  *B01L 3/00* (2006.01)
  *B42D 5/00* (2006.01)

(52) U.S. Cl.
  CPC . *B01L 2200/148* (2013.01); *B01L 2300/0825* (2013.01); *G01N 2001/024* (2013.01); *G01N 2001/028* (2013.01); *G01N 2001/2833* (2013.01)

(58) Field of Classification Search
  USPC .................................................... 73/864.71
  See application file for complete search history.

(56) References Cited

U.S. PATENT DOCUMENTS

| | | | |
|---|---|---|---|
| 5,741,984 A * | 4/1998 | Danylewych-May | ....................... A61B 10/0096 73/864 |
| 7,128,215 B2 | 10/2006 | Danechi | |
| 7,763,442 B2 * | 7/2010 | Martin | ..................... A61L 15/56 435/34 |
| 7,833,481 B2 * | 11/2010 | Eltomi | ..................... G01N 1/02 422/402 |
| 8,133,504 B2 | 3/2012 | Kettlewell et al. | |
| 8,183,053 B1 * | 5/2012 | Knobbe | ................. G01N 1/405 436/174 |
| 8,371,616 B2 | 2/2013 | Wu et al. | |
| 2006/0062689 A1 * | 3/2006 | Kirollos | ................. G01N 31/22 422/400 |
| 2006/0099649 A1 * | 5/2006 | Goh | ....................... B82Y 30/00 435/7.1 |
| 2007/0215725 A1 * | 9/2007 | Bunker | .................... G01N 1/02 239/551 |
| 2007/0289360 A1 * | 12/2007 | Horstmann | .............. A61B 5/00 73/23.35 |
| 2008/0057808 A1 * | 3/2008 | Simandl | ............... C11D 3/3749 442/59 |
| 2009/0197283 A1 * | 8/2009 | Gold | ..................... B01L 3/5029 435/7.9 |
| 2009/0243280 A1 | 10/2009 | Wu et al. | |
| 2011/0094514 A1 * | 4/2011 | Rakow | ................. A62B 18/088 128/206.12 |

FOREIGN PATENT DOCUMENTS

| | | |
|---|---|---|
| CN | 102252871 A | 11/2011 |
| EP | 1022554 A1 | 7/2000 |
| JP | 2005341870 A | 12/2005 |
| JP | 2008064618 A | 3/2008 |
| JP | 2008546715 A | 12/2008 |
| JP | 2011106926 A | 6/2011 |
| RU | 2130285 C1 | 5/1999 |
| RU | 2396985 C1 | 8/2010 |
| WO | 2007024323 A2 | 3/2007 |
| WO | 2014146197 | 9/2014 |

OTHER PUBLICATIONS

PCT/CA2014/050200 Search Report dated Apr. 28, 2014.
Extended European Search Report dated Sep. 12, 2016 for EP Appln. No. 14767829.6.
Office Action dated Dec. 19, 2017 for Japanese Application No. 2016-503498.
Office Action dated Sep. 6, 2017 for Mexican Application No. MX/a/2015/013290.
Office Action for Russian Application No. 2015/41381/15, dated Mar. 26, 2018.

* cited by examiner

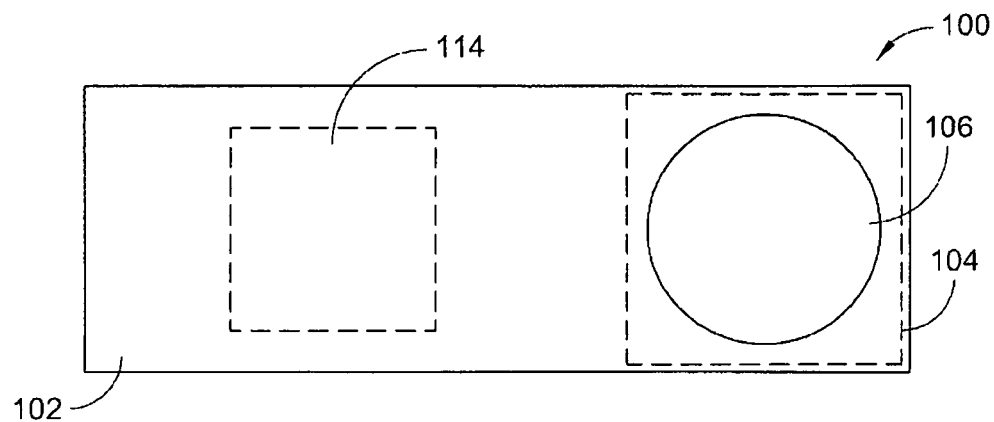
FIG. 1
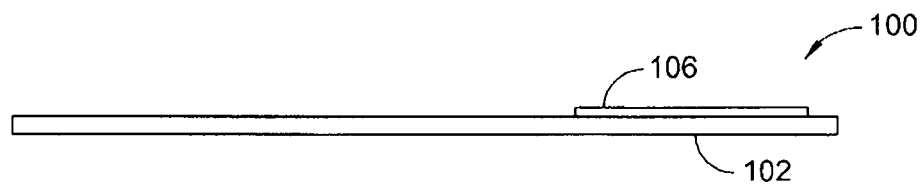
FIG. 2
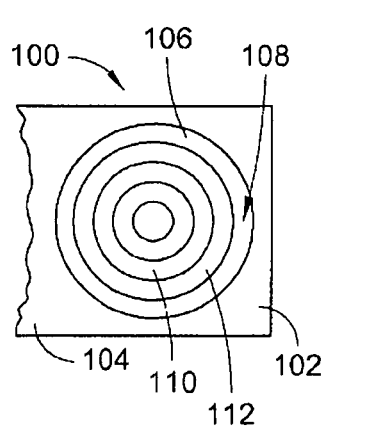 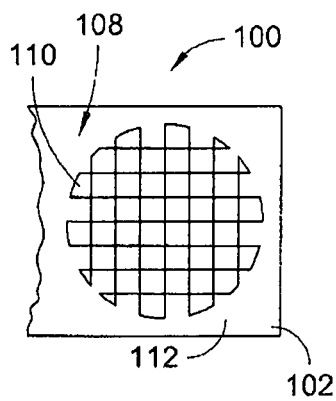 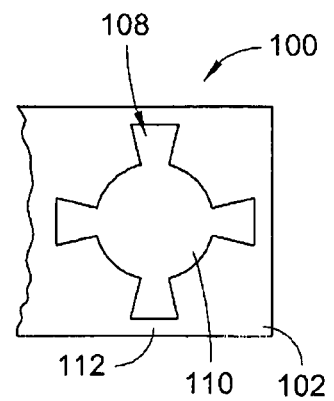
FIG. 3   FIG. 4   FIG. 5

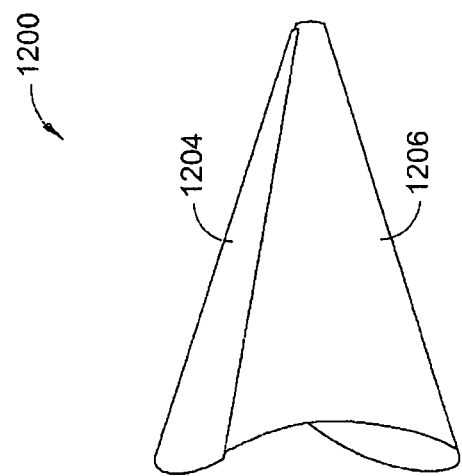
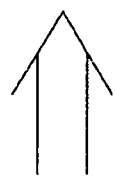
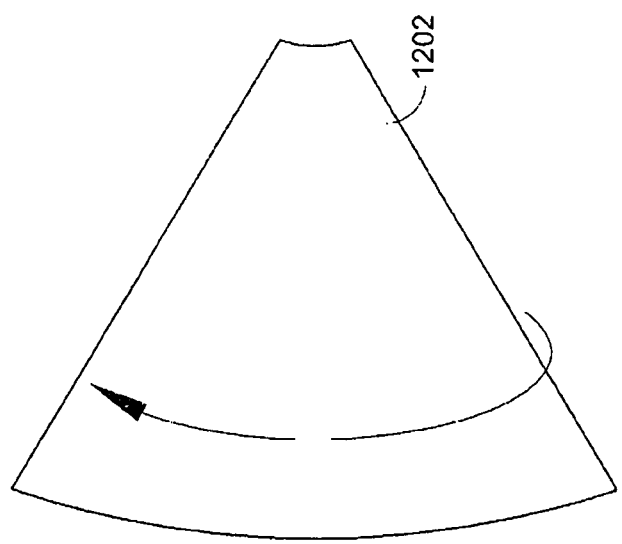
FIG. 12

TRACE ANALYTE COLLECTION SWAB

This application claims the benefit of U.S. Provisional Application No. 61/802,890, filed Mar. 18, 2013, titled "TRACE ANALYTE COLLECTION SWAB," which is herein incorporated by reference in its entirety.

BACKGROUND

Trace analyte detection is the detection of small amounts of analytes, often at nanogram to picogram levels. Trace analyte detection has numerous applications. For example, trace analyte detection can be particularly useful for security applications, such as screening individuals or items for components in explosive materials, narcotics or biological contaminants where small amounts of these components are deposited on the individual or on the outside of a package or bag. A variety of different techniques can be used for trace analyte detection. These methods include ion mobility spectrometry (IMS), mass spectrometry, gas chromatography, liquid chromatography, and high performance liquid chromatography (HPLC).

SUMMARY

A trace analyte collection swab having a collection surface at least partially coated with a microscopically tacky substance to enhance pick-up efficiency is described. In embodiments, the trace analyte collection swab comprises a substrate including a surface having a trace analyte collection area and a coating disposed on the surface of the substrate in the trace analyte collection area. The coating is configured to be microscopically adhesive to collect particles of the trace analyte from a surface when the trace analyte collection area is placed against the surface. In one embodiment, the coating comprises Polyisobutylene.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

FIG. 1 is a top plan view illustrating a trace analyte collection swab in accordance with an example embodiment of the present disclosure.

FIG. 2 is side elevation view of the trace analyte collection swab shown in FIG. 1.

FIGS. 3, 4, and 5 are partial top plan views illustrating trace analyte collection swabs in accordance with an example embodiment of the present disclosure, wherein the coating is patterned.

FIG. 12 is a top plan view illustrating a trace analyte collection swab in accordance with an example embodiment wherein the substrate comprises three-dimensional substrate having a generally triangular shape that is rolled into a cone prior to use.

DETAILED DESCRIPTION

Overview

Figure 6:
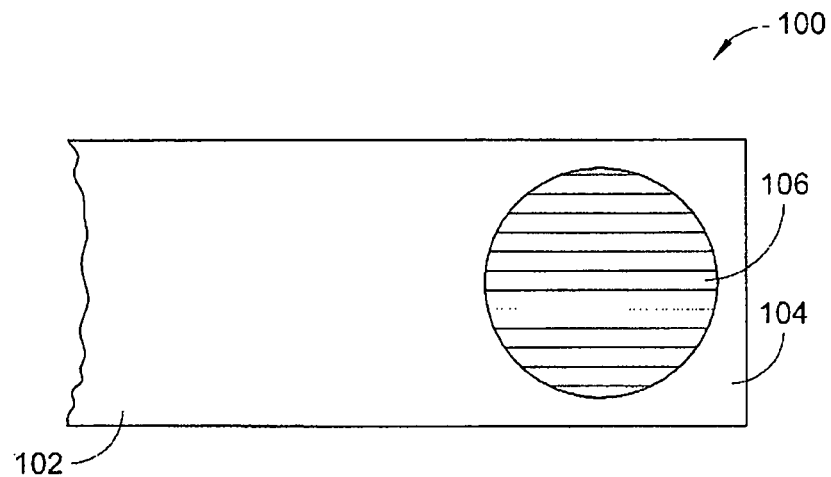
FIGS. 6 and 7 are partial top plan views illustrating trace analyte collection swabs in accordance with an example embodiment of the present disclosure, wherein the substrate has a first color and the coating has a second color different than the first color.

The collection (or harvesting) efficiency of trace analyte collection swabs varies for different chemicals being collected, for the swab material being used, and for different surfaces being swabbed. In some instances, the efficiency of collection of trace analytes from a surface using a conventional collection swab can be very low or zero for some chemicals. For example, where swabs made from NOMEX or Sharkskin materials are used to collect Trinitrotoluene (TNT), a dry chemical, from a vinyl (e.g., "leatherette") surface, the collection or harvesting efficiency is virtually zero (0) even at fifty (50) times the minimum alarm level capability of a conventional detector.

Consequently, it is desirable to improve the collection efficiency of conventional swabs. The National Institute for Science and Technology (NIST) described a method of increasing the collection efficiency of twenty-four micrometer (24 µm) polymeric spheres doped with one-half percent (0.5%) explosive. The method described used a tacky (to the touch) silicone material CV3-1161 manufactured by NuSil. NIST obtained significant improvement in pickup efficiency for the polymer spheres using the silicone tacky material. However, the use of NuSil CV3-1161 silicone at 5% loading on the swab surface leaves behind discernible streaks of silicone on the substrate surface following swabbing. When coating material is left behind on the sampled substrate, the collected explosive may also be left behind on the surface. Additionally, NuSil CV3-1161 and similar two-part adhesives are difficult to use, in that such two-part adhesives require that precise quantities of the polymer base and the catalyst be thoroughly mixed prior to application. Moreover, the catalyst must be stored at below freezing (<0 C) temperatures. Further, the pot-life of the mixed silicone adhesive is short—on the order of a few hours. Still further, the final coating of the adhesive must be cured at an elevated temperature. NuSil CV3-1161 and other 2-part adhesives also contain a peroxide catalyst which is a hazardous substance.

Accordingly, a trace analyte collection swab having a collection surface at least partially coated with a microscopically tacky substance to enhance pick-up efficiency is described. In embodiments, the trace analyte collection swab comprises a substrate including a surface having a trace analyte collection area and a coating disposed on the surface of the substrate in the trace analyte collection area. The coating is configured to be microscopically adhesive to collect particles of the trace analyte from a surface when the trace analyte collection area is placed against the surface.

In embodiments, the coating comprises Polyisobutylene (PIB). The coating may be applied in a pattern on the substrate in the trace particle collection area. The pattern may comprise one or more first areas where the coating is applied and one or more second areas where the coating is not applied. The one or more first areas are configured to collect particles of a trace analyte of a first type, while the one or more second areas are configured to collect particles of a trace analyte of a second type that are collected with a low collection efficiency, or that are not collected by the at least one first area. In embodiments, the substrate has a first color and the coating has a second color, wherein the second color is different than the first color.

In embodiments, the coating includes a dopant. The dopant may comprise a calibrating material for calibration of a detector. The dopant may comprise a reactant material configured to combine with a trace analyte when the swab is placed against a surface. The dopant may comprise a tracer material that can be used to indicate characteristics of the swab. The dopant may comprise a vapour-collecting material configured to collect particles of a trace analyte in vapour form.

In embodiments, the substrate comprises paper, filter paper (e.g., SHARKSKIN filter paper manufactured by Whatman Corporation), an aramid polymer material (e.g., NOMEX material manufactured by E.I. du Pont de Nemours and Company), and so forth. The substrate may be attached to a sampling wand. In other embodiments, the substrate comprises one or more bristles of a brush. The substrate may be provided with an identifier such as a barcode, Radio Frequency Identification (RFID) tag, and so forth, for furnishing identification of the swab. For example, in an embodiment, the substrate comprises a portion of a document such as a boarding pass, ticket, and so forth. The boarding pass may include an identifier such as a bar code configured to associate the particles of a trace analyte collected by the coating with the holder of the boarding pass. Similarly, in another embodiment, the substrate comprises a portion of package. The package may include a bar code configured to associate a trace analyte collected by the coating with the mailer and/or recipient of the package.

In embodiments, a plurality of substrates may be detachably joined together in a trace analyte collection swab dispensing system configured to dispense individual swabs.

Example implementations of trace analyte detection swabs will now be described with reference to the accompanying drawings.

Example Implementations

FIGS. 1 through 9 illustrate trace analyte collection swabs 100 in accordance with example embodiments of the present disclosure. As shown, the trace analyte collection swabs 100 comprise a substrate 102 including a surface having a trace analyte collection area 104 and a coating 106 disposed on the surface of the substrate 102 in the trace analyte collection area 104. In embodiments, the coating 106 may be disposed on the surface of the substrate 102 by coating the coating material onto the surface, depositing the coating material onto the surface, spraying the coating material onto the surface, soaking the coating material into the substrate 102 through the surface, combinations thereof, and so forth. Thus, a coating 106 disposed on the surface of the substrate 102 of a trace analyte collection swab 100 may be placed on the surface of the substrate 102 and/or may be soaked into the surface of the substrate 102.

In embodiments, the substrate 102 comprises a suitable substrate material such as paper, filter paper (e.g., SHARKSKIN filter paper manufactured by Whatman Corporation), an aramid polymer material (e.g., NOMEX material manufactured by E.I. du Pont de Nemours and Company), and so forth. The substrate 102 may be configured to be received by a chemical/explosives detector which may employ any of a variety of detection technologies including: ion mobility spectrometry (IMS), mass spectrometry, gas chromatography, liquid chromatography, high performance liquid chromatography (HPLC), combinations thereof, and so forth. For example, in the embodiment shown, the substrate 102 comprises a generally rectangular strip of the substrate material (e.g., paper, filter paper, aramid polymer material, etc.) which may be placed against a surface to collect particles of one or more trace analytes, and then inserted into a detector where collected particles are desorbed. In a specific example of this embodiment, the substrate 102 may comprise a strip of substrate material having a length of 6.35 cm (2.5 in) and a width of 2.54 cm (1 in). In this example, the substrate material may comprise paper having a paper weight of approximately 80 gsm (20 lb). However, it is contemplated that the substrate material may comprise papers having paper weights greater or less than 80 gsm (20 lb). Moreover, it is contemplated that the substrate material may also comprise filter paper, an aramid polymer material, combinations thereof, and so forth. Further, it is contemplated that the substrate 102 may have other shapes (e.g., square, oval, triangular, circular, irregular, etc.). The surface of the substrate 102 can be smooth or roughened.

In embodiments, the substrate 102 may be configured for attachment to a sampling wand. For example, an adhesive may be disposed on the surface of the substrate opposite the coating 106 (e.g., on the reverse side of the trace analyte collection area 104 of the substrate 102) to facilitate attachment of the swab 100 to and/or removal of the swab 100 from a sampling wand (not shown).

The coating 106 is configured to be microscopically adhesive to collect particles of the trace analyte from a surface when the trace analyte collection area 104 is placed (e.g., pressed) against the surface. In embodiments, the coating comprises Polyisobutylene (PIB) having a formulation such as PIB 4T or other PIB formulations. The PIB may have a molecular weight of approximately 59,000 GPC (Gel Permeation Chromatography). FIB (e.g., PIB 4T or other PIB formulation) is not hazardous to humans or animals, can be stored at room temperature indefinitely, readily dissolves in hexane, is stable in solution, and has substantially no pot-life.

The coating 106, which, in embodiments, comprises PIB (e.g., PIB 4T or other PIB formulation), is not perceptibly tacky or sticky (e.g., the coating 106 is dry-to-the-feel) and does not adhere to the surface being sampled, but is microscopically adhesive (e.g., microscopically sticky or tacky) to particles of the trace analyte. Additionally, the coating 106 leaves no residue when the trace analyte collection area 104 is placed against the surface to be swabbed. For dry particles, the coating 106 improves the collection (pick-up or "harvesting") efficiency of the swab 100 from the surface being swabbed compared to swabs that are not provided with the coating 106. The coating 106 microscopically adheres the collected particles of the trace analyte to the swab 100 so that collected particles do not become dislodged and fall from the swab 100 during detection. Moreover, the coating 106 may retain volatile trace chemicals that would otherwise rapidly evaporate. The coating 106 withstands exposure to high temperatures without degradation, permitting use of the trace analyte collection swab 100 with a heated detector. Further, the coating, when heated, has limited or no outgassing of volatile materials that might otherwise contaminate a collected sample.

In embodiments, the coating 106 comprises a dopant such as a trace chemical that may be subsequently released during desorption by the detector. It is contemplated that a variety of dopants may be applied to the coating 106. For example, in an embodiment, the dopant may comprise a calibrating material for calibration of a detector. In another embodiment, the dopant may comprise a reactant material configured to combine with the particles of trace analyte when the swab 100 is placed against a surface to be sampled. The reactant material may, for example, help to collect particles of a trace analyte from a surface, help to adhere particles of a trace analyte to the swab 100, and/or help to desorb particles of a trace analyte from the swab 100. In another embodiment, the dopant may comprise a vapour-collecting material configured to collect particles of the trace analyte in vapour form which are subsequently released upon heating or desorption. Example vapour-adsorbing materials include charcoal, a chromatographic absorption material such as TENAX, and so forth. In another embodiment, the dopant may comprise a tracer material that can be used to indicate characteristics of the swab 100 when desorbed. For example, the coating 106 may be doped with a tracer material to verify the authenticity of the swab 100. The coating 106 may also be doped with a tracer material to indicate the suitability of the swab for collecting the trace analyte. The coating may further be doped with a tracer material that indicates the life of the swab 100 in multiple use applications (e.g., indicates when the swab 100 has exceeded its useful life). The coating 106 may also be doped with a tracer material to furnish a valid minimum response when used in combination with a detector to indicate correct operation of the detector.

In embodiments, the coating 106 is applied over a limited portion (e.g., area) of the trace analyte collection area 104 so that collected particles of trace analyte are concentrated for delivery to a detector for desorption of the trace analyte. For example, the position and area covered by the coating 106 may at least substantially match the position and area of the inlet opening of the detector with which the swab 100 is used. In the embodiment illustrated in FIG. 1, the coating 106 is applied over a circular area of the trace analyte collection area 104 of the substrate 102. In one specific example, the circular area has a diameter of approximately 1.905 cm (0.75 in). However, it is contemplated that the portion of the substrate 102 over which the coating 106 is applied may have other shapes and surface areas.

In embodiments, the coating 106 is applied in a pattern 108 on the substrate 102 in the trace particle collection area 104. FIGS. 3, 4, and 5 illustrate example trace analyte collection swabs 100, wherein the coating 106 is patterned. As shown, the pattern 108 may comprise one or more first areas 110 where the coating 106 is applied and one or more second areas 112 where the coating is not applied. The one or more first areas 110 are configured to collect particles of a trace analyte of a first type, while the one or more second areas are configured to collect particles of a trace analyte of a second type. Thus, for example, the coating 106 may be applied to one or more first areas 110 to collect particles of dry chemicals such as TNT which do not efficiently adhere to the uncoated swab surface, while the second areas 112 where the coating is not applied may collect particles of sticky trace chemicals that adhere to the uncoated swab surface more efficiently than to the coating 106, or do not adhere to the coating 106. Additionally, the second areas 112 allow the swab surface to be exposed so that the swab material, which may be absorbent, can wick away traces of moisture that might otherwise contaminate or suppress the collection of trace analytes. Moreover, patterning of the coating 106 can facilitate printing of indicia such as, directions for use of the swab, a barcode, a logo or other marketing information, and so forth. FIGS. 3, 4 and 5 illustrate different coating patterns 108. In FIG. 3, the coating 106 is patterned so that the first areas 110 and the second areas 112 comprise interspersed concentric rings (e.g., the coating 102 is patterned in a "target" pattern). In FIG. 4, the first areas 110 and the second areas 112 are arranged in alternating squares (e.g., the coating 106 is patterned in a "checkerboard" pattern 108). In FIG. 5, the first areas 110 and the second areas 112 are patterned in alternating strips (e.g., the coating 106 is patterned in a spaced-apart bar pattern 108). Other patterns 108 may also be employed.

Figure 7:
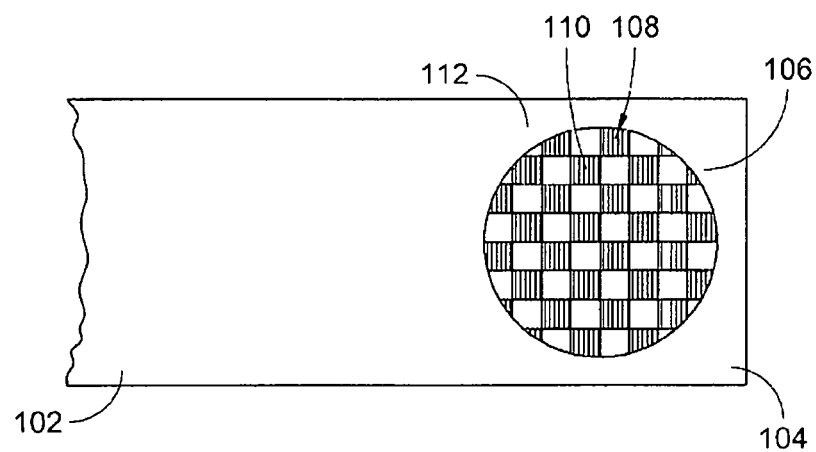

In embodiments, the coating 106 may be clear or translucent. In other embodiments, the coating 106 may be tinted so that the substrate 102 may have a first color and the coating 106 may have a second color, wherein the second color is different than the first color. In this manner, coating 106 of the swab 100 may function to indicate which side of the swab 100 to use to collect a sample, the location on the substrate 102 to which to apply swabbing pressure (e.g., on the surface opposite the coating 106 behind the trace analyte collection area 104), the correct location of the swab 100 in a sampling wand, and so forth. FIGS. 6 and 7 illustrate example trace analyte collection swabs 100, wherein the substrate 102 has a first color and the coating 106 has a second color different than the first color. In FIG. 6, the coating 106 is applied over a circular area and is shown as being tinted blue against a white substrate 102. In FIG. 7, the coating 106 is patterned with a checkerboard pattern 108 having first areas 110 provided with the coating 106 and second areas 112 without the coating 106. The coating 106, applied in the second areas 112 is shown as being tinted red against a white substrate 102 in the first areas 110. However, it is contemplated that the coating 106 may be tinted in other colors, combinations of colors (e.g., green and yellow, red and blue, a multicolored logo, etc.), and so forth.

In embodiments, the substrate 102 of the trace analyte collection swab 100 may be provided with an identifier 114, which may be machine readable, such as a barcode, a Radio Frequency Identification (RFID) tag or patch, identification indicia, combinations thereof, and so forth, for furnishing identification of the swab 100. For example, in FIG. 1, the substrate 102 is illustrated as including an identifier 114 comprised of a two dimensional (2D) barcode. In embodiments, the identifier 114 may be used to verify the authenticity of the swab 100, to indicate the suitability of the swab for collecting the trace analyte, to indicate the life of the swab 100 in multiple use applications (e.g., indicates when the swab 100 has exceeded its useful life), and so forth.

Figure 8:
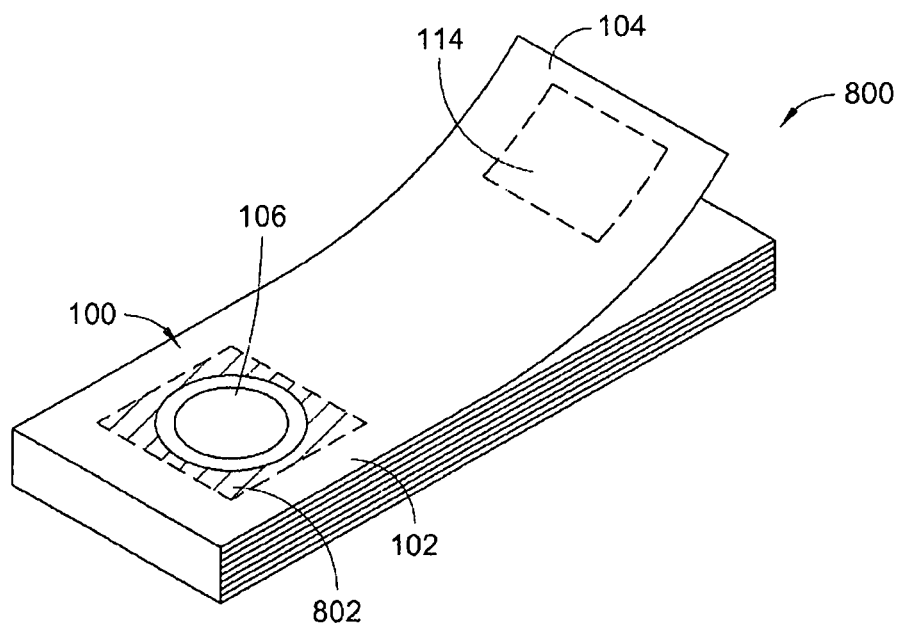
FIG. 8 is an isometric view illustrating a trace analyte collection swab dispensing system in accordance with an example embodiment of the present disclosure, wherein a releasable adhesive is disposed on the surfaces of respective substrates to detachably join the respective substrates to an adjacent substrate in a stacked configuration.
Figure 9:
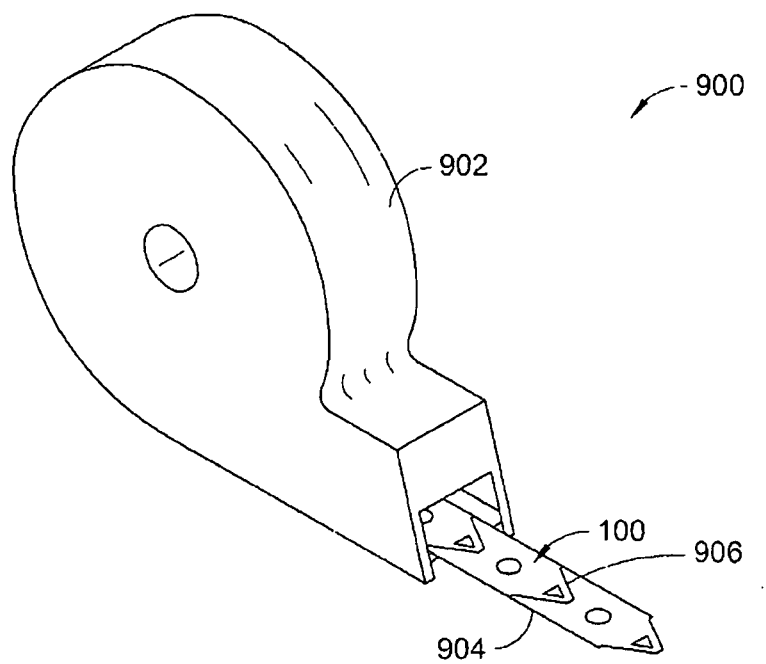
FIG. 9 is an isometric view illustrating a trace analyte collection swab dispensing system in accordance with an example embodiment of the present disclosure, wherein a plurality of substrates are attached in a roll, and wherein respective ones of the plurality of substrates are joined end-to-end via a perforated section within the roll.

In embodiments, a plurality of substrates 102 may be detachably joined together in a trace analyte collection swab dispensing system configured to dispense individual swabs 100. FIGS. 8 and 9 illustrate trace analyte collection swab dispensing systems 800, 900 in accordance with example embodiments of the present disclosure.

In the embodiment shown in FIG. 8, the trace analyte collection swab dispensing system 800 comprises a plurality of substrates 102 detachably joined together in a stacked arrangement. For example, a releasable adhesive 802 may be applied to an end portion of the surfaces of respective substrates 102 opposite the trace analyte collection area 104 and coating 106 (e.g., the backside of the swab 100). However, it is contemplated that, in embodiments, the coating 106 could be made sufficiently tacky to join the substrates 102 together without the use of an additional releasable adhesive 802. The releasable adhesive 802 (or tacky coating 106) is configured to detachably join the bottom surface respective substrates 102 to the top surface of an adjacent substrate 102 in the stacked arrangement. In this manner, the surface of the substrate 102 on which the coating 106 is disposed is occluded and thus protected from contamination. By occluding or protecting the surface of the substrate 102 containing the coating 106, the cleaning processes typically employed for cleaning raw-material swabs in order to make them suitable for use as a trace detection swab may be reduced or eliminated.

As shown in FIG. 8, the substrates 102 of the respective trace analyte collection swabs 100 may be provided with an identifier 114, which may be machine readable, such as a barcode, an RFID tag or patch, identification indicia, combinations thereof, and so forth, for furnishing identification of the swab 100. In embodiments, the identifier 114 may be used to verify the authenticity of a swab 100 when dispensed, to indicate the suitability of the swab for collecting the trace analyte, and so forth. In embodiments, the substrates 102 of the respective trace analyte collection swabs 100 may be configured for attachment to a sampling wand. For example, an adhesive may be disposed on the surface of the respective substrates 102 opposite the coating 106 (e.g., on the reverse side of the trace analyte collection area 104 of the substrate 102) to facilitate attachment of the swab 100 to and/or removal of the swab 100 from a sampling wand (not shown).

In the embodiment shown in FIG. 9, the trace analyte collection swab dispensing system 900 comprises a dispensing apparatus 902 containing a roll 904 of trace analyte collection swabs 100, wherein the respective substrates 102 of the swabs 100 are joined end-to-end via a perforated section 906 (which may be generally V-shaped) within the roll 904. The perforated sections 906 allow individual swabs 100 to be separated from the roll 904 for use. Again, the surface of the substrate 102 on which the coating 106 is disposed is occluded and thus protected from contamination so that the cleaning processes typically employed for cleaning raw-material swabs in order to make them suitable for use as a trace detection swab may be reduced or eliminated.

Figure 10:
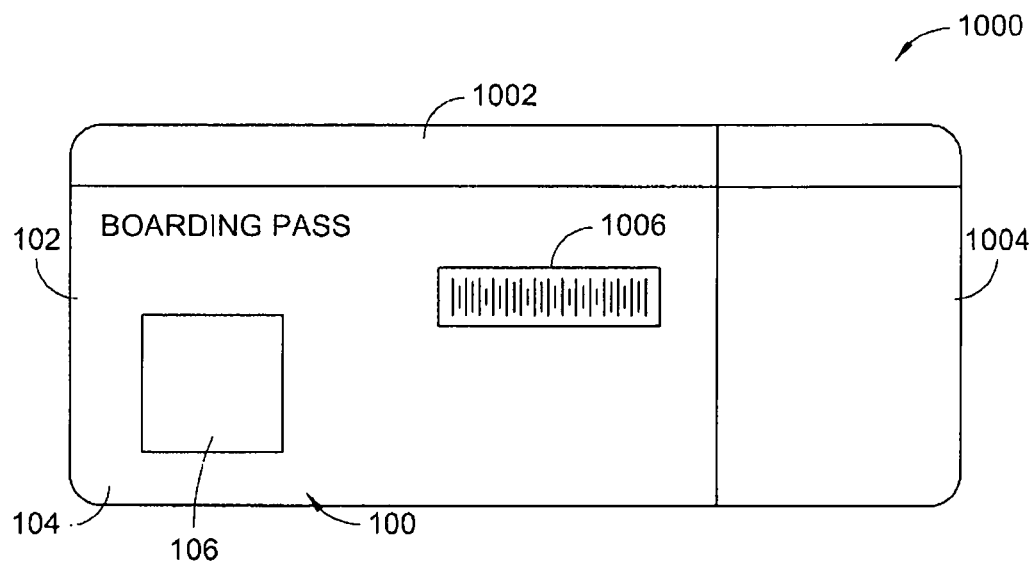
FIG. 10 is an isometric view illustrating a trace analyte collection swab in accordance with an example embodiment of the present disclosure, wherein the substrate of the trace analyte collection swab comprises a portion of a document such as an airline boarding pass, a ticket, and so forth.

The trace analyte collection swab 100 may be fabricated as part of, or may be attached to, another item or device that could be handled by an individual leaving trace materials. In embodiments, the trace analyte collection swab 100 may comprise a portion of, or may be attached to, a document such as an airline boarding pass, a ticket, and so forth. For example, as shown in FIG. 10, the substrate 102 of the trace analyte collection swab 100 is illustrated as comprising a portion of an airline boarding pass 1000. In the embodiment illustrated, the boarding pass 1000, or a portion thereof, is fabricated of a suitable substrate material as described above and may include a portion 1002 that is retained by the airline, a governmental body such as the United States Transportation Security Administration (TSA), and so forth, and a portion 1004 that is provided to the traveler prior to boarding an aircraft. As shown, the retained portion 1002 includes a trace analyte collection area 104 positioned in an area of the boarding pass likely to be handled by the traveler and a coating 106 disposed on the surface of the substrate 102 in the trace analyte collection area 104 to collect trace analytes from the hands of the traveler for detection and/or analysis. In other embodiments, the trace analyte collection swab 100 may comprise a portion of the boarding pass 1000 that is removed and retained by the airline, governmental body, and so forth (e.g., a peelable sticker, a perforated section, and so forth), such as for analysis. The boarding pass 1000 may further include an identifier 1006 such as a bar code, RFID tag or patch, or the like, configured to associate the particles of a trace analyte collected by the coating 106 with the holder of the boarding pass 1000.

Figure 11:
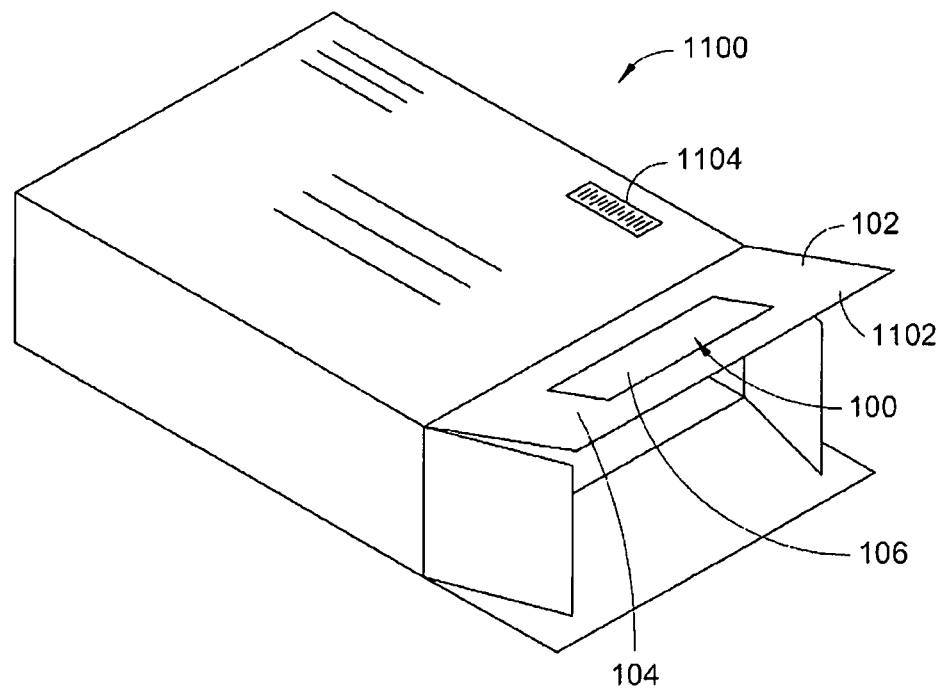
FIG. 11 is an isometric view illustrating a trace analyte collection swab in accordance with an example embodiment of the present disclosure, wherein the substrate of the trace analyte collection swab comprises a portion of a package.

In other embodiments, the trace analyte collection swab 100 may comprise a portion of, or be attached to, a mailed item such as an envelope, package, and so forth. For example, as shown in FIG. 11, the substrate 102 of the trace analyte collection swab 100 is illustrated as comprising a portion of a package 1100. In the embodiment illustrated, the package 1100, or a portion thereof such as a flap 1102, is fabricated of a suitable substrate material as described above. However, in other embodiments, the substrate 102 may be adhered to the package 1100 (e.g., via a peelable sticker, address label, stamp, and so forth), which may later be removed from the package 1100, such as for analysis. As shown, the package 1100 includes a trace analyte collection area 104 (e.g., flap 1102) positioned in a portion of the package likely to be handled by the mailer (e.g., a person depositing the package in the mail, a person handling the package prior to mailing, and so forth) when sealing the package and a coating 106 disposed on the surface of the substrate 102 in the trace analyte collection area 104 to collect trace analytes from the hands of the mailer for detection and/or analysis. In embodiments, the package 1100 may further include an identifier 1106 such as a bar code, RFID tag or patch, or the like, configured to associate the particles of a trace analyte collected by the coating 106 with the mailer and/or a recipient of the package 1100.

In the embodiments described above, the substrate 102 of the trace analyte collection swab has comprised a generally flat sheet of substrate material. However, it is contemplated that the substrate 102 need not necessarily be limited to this form factor. For example, the substrate 102 may be formed of a sheet of substrate material that is shaped (e.g., folded, rolled, embossed, etc.) into a three dimensional shape (e.g., a cylinder, a cone, etc.). When formed into a three dimensional shape, the substrate 102 may be attached to a sampling wand, which may be configured to allow the trace analyte collection swab 100 to be rolled against a surface to collect analyte from the surface.

For example, FIG. 12 illustrates a trace analyte collection swab 1200 that includes a substrate 1202 that is generally triangular (e.g., pie-shaped). As shown, the substrate 1202 may be rolled into a cone having an outer surface that forms the trace analyte collection area 1204 and a coating 1206 disposed on the substrate 1202 (e.g., on the outer surface of the cone) in the trace analyte collection area 1204.

Figure 13:
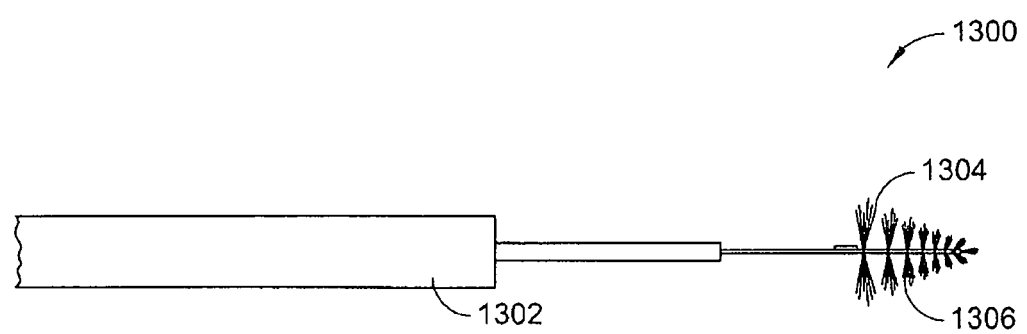
FIG. 13 is a top plan view illustrating a trace analyte collection swab in accordance with an example embodiment of the present disclosure, wherein the swab comprises a brush.

Additionally, it is contemplated that non-sheet form factor substrates 102 may be used. For example, shown in FIG. 13, the trace analyte collection swab 1300 illustrated comprises a brush 1302. In this embodiment, the substrate is comprised of the bristles 1304 of the brush 1302, which may be coated with a coating 1304 for collection of particles of trace analyte from a surface. The coating 1306 is configured to be microscopically adhesive to collect particles of the trace analyte from a surface when the bristles 1304 of the brush are placed (e.g., brushed) against the surface. In embodiments, the coating comprises Polyisobutylene (PIB) having a formulation such as PIB 4T or other PIB formulations. The PIB may have a molecular weight of approximately 59,000 GPC (Gel Permeation Chromatography). PIB (e.g., PIB 4T or other PIB formulation) is not hazardous to humans or animals, can be stored at room temperature indefinitely, readily dissolves in hexane, is stable in solution, and has substantially no pot-life.

The coating 1306, which, in embodiments, comprises PIB (e.g., PIB 4T or other PIB formulation), is not perceptibly tacky or sticky (e.g., the coating 106 is dry-to-the-feel) and does not adhere to the surface being sampled, but is microscopically adhesive (e.g., microscopically sticky or tacky) to particles of the trace analyte. Additionally, the coating 1306 leaves substantially no residue when the bristles 1304 of the brush are placed (e.g., brushed) against the surface to be swabbed. The coating 1306 thus improves the collection (pick-up or "harvesting") efficiency of the swab 1300 from the surface being swabbed compared to swabs that are not provided with the coating 1306. The coating 1306 microscopically adheres the collected particles of the trace analyte to the bristles 1304 of the swab 1300 so that collected particles do not become dislodged and fall from the swab 1300 during detection. Moreover, the coating 1306 may retain particles of volatile trace chemicals that would otherwise evaporate. The coating 1306 withstands exposure to high temperatures without degradation, permitting use of the trace analyte collection swab 1300 with a heated detector. Further, the coating, when heated, has limited or no outgassing of volatile materials that might otherwise contaminate a collected sample.

In embodiments, the coating 1306 comprises a dopant such as a trace chemical that may be subsequently released during desorption by the detector. It is contemplated that a variety of dopants may be applied to the coating 1306. For example, in an embodiment, the dopant may comprise a calibrating material for calibration of a detector. In another embodiment, the dopant may comprise a reactant material configured to combine with the particles of trace analyte when the swab 1300 is placed against a surface to be sampled. The reactant material may, for example, help to collect particles of a trace analyte from a surface, help to adhere particles of a trace analyte to the swab 1300, and/or help to desorb particles of a trace analyte from the swab 1300. In another embodiment, the dopant may comprise a vapour-collecting material configured to collect particles of the trace analyte in vapour form which are subsequently released upon heating or desorption. Example vapour-collecting materials include charcoal, a chromatographic absorption material such as TENAX, and so forth. In another embodiment, the dopant may comprise a tracer material that can be used to indicate characteristics of the swab 1300 when desorbed. For example, the coating 1306 may be doped with a tracer material to verify the authenticity of the swab 1300. The coating 1306 may also be doped with a tracer material to indicate the suitability of the swab for collecting the trace analyte. The coating may further be doped with a tracer material that indicates the life of the swab 1300 in multiple use applications (e.g., indicates when the coating 100 has exceeded its useful life). The coating 1306 may also be doped with a tracer material to furnish a valid minimum response when used in combination with a detector to indicate correct operation of the detector.

In embodiments, the brush 1302 can be capped so that particles of trace analyte collected remotely can be protected from subsequent contamination. The brush 1302 may be capable of reuse (e.g., following a suitable cleaning process). In embodiments, the brush 1302 is inserted into the inlet area of a detector directly, and heated radiatively or through convection. In other embodiments, the material from which the bristles 1304 of the brush 1302 are fabricated may be conductive to allow for resistive heating of the coated bristles 1304, providing increased control over the heating process. In this manner, heating at higher temperatures than would be achieved using a heated inlet may be possible. Additionally, the use of resistive heating may allow for temperature ramping at a much greater rate than is achievable using a ramped-temperature or fixed temperature inlet. In this manner, the release of the collected particles of trace analyte as vapour would be faster than with a ramped-temperature or fixed temperature inlet, providing a higher signal amplitude, and thus a better limit of detection.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A trace analyte collection swab comprising:
   a swab substrate comprising a surface having a trace analyte collection area; and
   a coating disposed on the surface of the swab substrate in the trace analyte collection area, the coating configured to be dry-to-the-feel and not perceptibly tacky yet microscopically adhesive to collect particles of the trace analyte from a surface when the trace analyte collection area is placed against the surface, the coating being applied in a pattern on the swab substrate in the trace particle collection area;
   wherein the pattern comprises at least one first area where the coating is applied and at least one second area where the coating is not applied, the at least one first area configured to collect particles of a trace analyte of a first type and the at least one second area configured to collect particles of a trace analyte of a second type that are not collected by the at least one first area.

2. The trace analyte collection swab as recited in claim 1, wherein the coating comprises Polyisobutylene.

3. The trace analyte collection swab as recited in claim 1, wherein the swab substrate has a first color and the coating has a second color, the second color being different than the first color.

4. The trace analyte collection swab as recited in claim 1, wherein the coating comprises a dopant.

5. The trace analyte collection swab as recited in claim 4, wherein the dopant comprises a calibrating material, a reactant material, a tracer material, or a vapour-collecting material.

6. The trace analyte collection swab as recited in claim 1, wherein the swab substrate comprises an identifier configured to furnish identification of the trace analyte collection swab.

7. The trace analyte collection swab as recited in claim 1, wherein the swab substrate comprises a boarding pass, the boarding pass including a bar code, the bar code configured to associate the particles of the trace analyte collected by the coating with a holder of the boarding pass.

8. The trace analyte collection swab as recited in claim 1, wherein the swab substrate comprises a package including a bar code, the bar code configured to associate the particles of the trace analyte collected by the coating with a mailer of the package.

9. A trace analyte collection swab dispensing system comprising:
a plurality of swab substrates detachably joined together, respective ones of the plurality of swab substrates comprising a surface having a trace particle collection area; and
a coating disposed on the surfaces of the respective swab substrates in the trace particle collection areas, the coating configured to be dry-to-the-feel and not perceptibly tacky yet microscopically adhesive to collect particles of the trace analyte from a surface when the trace particle collection area is placed against the surface, the coating being applied in a pattern on the swab substrate in the trace particle collection area;
wherein the pattern comprises at least one first area where the coating is applied and at least one second area where the coating is not applied, the at least one first area configured to collect particles of a trace analyte of a first type and the at least one second area configured to collect particles of a trace analyte of a second type that are not collected by the at least one first area.

10. The trace analyte collection swab dispensing system as recited in claim 9, wherein the coating comprises Polyisobutylene.

11. The trace analyte collection swab dispensing system as recited in claim 9, further comprising a releasable adhesive disposed on the surfaces of respective swab substrates, the releasable adhesive configured to detachably join the respective swab substrates to an adjacent swab substrate.

12. The trace analyte collection swab dispensing system as recited in claim 9, wherein the plurality of swab substrates are attached in a roll, wherein respective ones of the plurality of swab substrates are joined end-to-end via a perforated section within the roll.

13. A trace analyte collection swab comprising:
a swab substrate including a surface having a trace particle collection area; and
a coating of Polyisobutylene disposed on the surface of the swab substrate in the trace particle collection area, the coating configured to be dry-to-the-feel and not perceptibly tacky yet microscopically adhesive to collect particles of the trace analyte from a surface when the trace particle collection area is placed against the surface;
wherein the coating is applied in a pattern on the swab substrate in the trace particle collection area, the pattern comprising at least one first area where the coating is applied and at least one second area where the coating is not applied, the at least one first area configured to collect particles of a trace analyte of a first type and the at least one second area configured to collect particles of a trace analyte of a second type that are not collected by the at least one first area.

14. The trace analyte collection swab as recited in claim 13, wherein the coating comprises a dopant.

15. The trace analyte collection swab as recited in claim 14, wherein the dopant comprises a calibrating material, a reactant material, a tracer material, or a vapour-collecting material.

16. The trace analyte collection swab as recited in claim 13, wherein the swab substrate comprises a boarding pass, the boarding pass including a bar code, the bar code configured to associate the particles of the trace analyte collected by the coating with a holder of the boarding pass.

17. The trace analyte collection swab as recited in claim 13, wherein the swab substrate comprises a package including a bar code, the bar code configured to associate the particles of the trace analyte collected by the coating with a mailer of the package.

18. The trace analyte collection swab as recited in claim 13, wherein the swab substrate comprises a three-dimensional (3D) shaped swab substrate.

* * * * *